(12) United States Patent
Scholz

(10) Patent No.: US 9,738,939 B2
(45) Date of Patent: Aug. 22, 2017

(54) METHOD FOR DIFFERENTIATING BETWEEN LIVING AND DEAD CELLS

(71) Applicant: Sartorius Stedim Biotech GmbH, Göttingen (DE)

(72) Inventor: Alexandra Scholz, Göttingen (DE)

(73) Assignee: Sartorius Stedim Biotech GmbH (DE)

( * ) Notice: Subject to any disclaimer, the term of this patent is extended or adjusted under 35 U.S.C. 154(b) by 389 days.

(21) Appl. No.: 14/416,463

(22) PCT Filed: May 27, 2013

(86) PCT No.: PCT/EP2013/001564
§ 371 (c)(1),
(2) Date: Jan. 22, 2015

(87) PCT Pub. No.: WO2014/015925
PCT Pub. Date: Jan. 30, 2014

(65) Prior Publication Data
US 2015/0203898 A1    Jul. 23, 2015

(30) Foreign Application Priority Data

Jul. 26, 2012   (DE) .................. 10 2012 014 981

(51) Int. Cl.
*C12Q 1/68* (2006.01)

(52) U.S. Cl.
CPC ........... *C12Q 1/689* (2013.01); *C12Q 1/6844* (2013.01); *C12Q 1/6851* (2013.01); *C12Q 2600/158* (2013.01)

(58) Field of Classification Search
None
See application file for complete search history.

(56) References Cited

FOREIGN PATENT DOCUMENTS

| | | |
|---|---|---|
| EP | 2077334 A1 | 7/2009 |
| WO | WO 03/072805 A2 | 9/2003 |

OTHER PUBLICATIONS

Rudi et al. Applied and Environmental Microbiology 2005; 71: 1018-1024.*
Beckhoven et al., "Detection of *Clavibacter michiganensis* subsp. Sepedonicus by AmpliDet RNA, a new technology based on real time monitoring of NASBA amplicons with a molecular beacon", *Journal of Applied Microbiology 93*, 840-849 (2002).
Bentsink et al., "Amplification of RNA by NASBA allows direct detection of viable cells of *Ralstonia solanacearum* in potato", *Journal of Applied Microbiology 93*, 647-655 (2002).
Chen et al., "Rapid Detection of Viable Salmonellae in Produce by Coupling Propidium Monoazide with Loop-Mediated Isothermal Amplification", *Applied and Environmental Microbiology*, vol. 77 (12), 4008-4016 (2011).
Cook et al., "The use of NASBA for the detection of microbial pathogens in food and environmental samples", *Journal of Microbiological Methods 53*, 165-174 (2003).
International Search Report for PCT/EP2013/001564, 4 pages, Nov. 29, 2013.
Josefsen et al., "Rapid Quantification of Viable Campylobacter Bacteria on Chicken Carcasses, Using Real-Time PCR and Propidium Monoazide Treatment, as a Tool for Quantitative Risk Assessment", *Applied and Environmental Microbiology*, vol. 76 (15), 5097-5104 (2010).
Min et al., "Highly Sensitive and Specific Detection of Viable *Escherichia coli* in Drinking Water", *Analytical Biochemistry 303*, 186-193 (2002).
Piepenburg et al., "DNA Detection Using Recombination Proteins", *PLOS Biol 4* (7), e204, 1115-1121 (2006).
Yamazaki et al., "Development of a loop-mediated Isothermal amplification assay for sensitive and rapid detection of Vibrio parahaemolyticus", *BMC Microbiology 8*, 163, 7 pages (2008).

* cited by examiner

*Primary Examiner* — Angela M Bertagna
(74) *Attorney, Agent, or Firm* — Viksnins Harris Padys Malen LLP

(57) ABSTRACT

The present invention relates to a method for quantitatively determining living and dead cells in a biological sample. The method according to the present invention is based on the determination of the amount of DNA in the sample with the aid of a DNA amplification reaction which does not impair the membrane integrity of living cells.

12 Claims, 6 Drawing Sheets

SEQUENCE LISTING

```
<160> NUMBER OF SEQ ID NOS: 2

<210> SEQ ID NO 1
<211> LENGTH: 35
<212> TYPE: DNA
<213> ORGANISM: Artificial sequence
<220> FEATURE:
<223> OTHER INFORMATION: Primer

<400> SEQUENCE: 1
caggattaga taccctggta gtccacgccg taaac                          35

<210> SEQ ID NO 2
<211> LENGTH: 35
<212> TYPE: DNA
<213> ORGANISM: Artificial sequence
<220> FEATURE:
<223> OTHER INFORMATION: Primer

<400> SEQUENCE: 2
taaggggcat gatgatttga cgtcatcccc acctt                          35
```

METHOD FOR DIFFERENTIATING BETWEEN LIVING AND DEAD CELLS

CROSS REFERENCE TO RELATED APPLICATIONS

Figure 1:
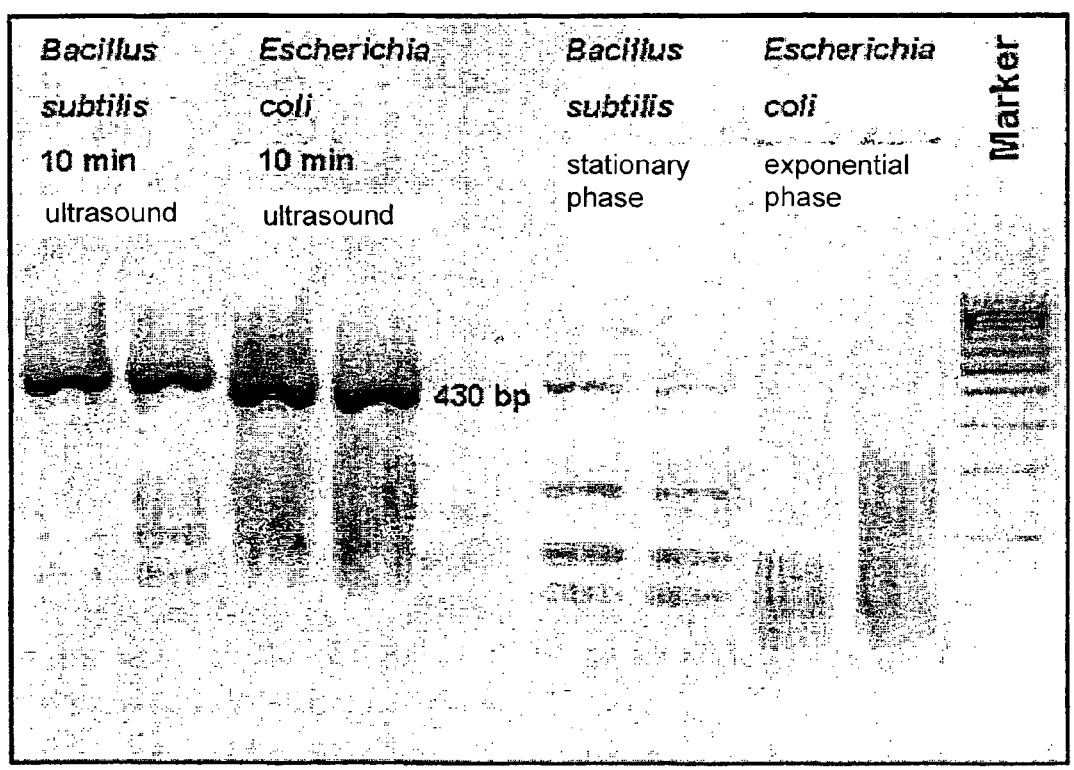

This patent application claims the benefit of priority of German Application Serial No. 10 2012 014 981.6, filed Jul. 26, 2012.

The present invention relates to a method for quantitatively determining living and dead cells in a biological sample. The method according to the present invention is based on the determination of the amount of DNA in the sample with the aid of a DNA amplification reaction which does not impair the membrane integrity of living cells.

In the context of many problems, for example, in the medical, pharmaceutical or food technological field, it is a matter of interest not only to detect the presence of, for example, contaminating bacteria in samples, but also to be able to make quantitative statements whether optionally present bacteria are viable. Besides traditional microscopical and/or microbiological methods, the power of which is not in the field of high sensitivity or quickness, the molecular diagnostic based on the polymerase chain reaction (PCR) in many variants has developed to a standard tool. However, with the aid of the "standard PCR", no differentiation between living/dead can be achieved, since both DNA of living and dead cells is amplified and thus detected.

A group of PCR-supported detection methods implements the principle of a differentiation between genomic DNA from living and dead cells by using intercalation compounds, for example, based on ethidium or propidium azides, like ethidium monoazide (EMA) or propidium monoazide (PMA), which selectively intrude in dead cells having a defective membrane integrity and render their DNA inaccessible for a PCR amplification by covalently binding to the same. Subsequently, only the DNA of the at last living cells can be selectively reproduced. This principle of selective fluorescence dyes, which act as DNA intercalators, is known, for example, from WO 2007/100762 A2, EP 1 992 690 A1, US 2009/0123959 A1, WO 2011/043737 A1, WO 2011/068465 A1, WO 2007/064313 A1, US 2011/0318750 A1, EP 2 077 334 A1 and CA 2 768 699 A1.

Meanwhile, EMA/PMA-PCR and related methods are used in food technology as well as for analysis of environmental samples. However, the precision of the results obtained by EMA/PMA-PCR is diminished in many cases, for example, by influencing follow-up analyses due to EMA/PMA residues, which act in an inhibiting manner on PCR reactions and have to be removed in the framework of a DNA isolation, as well as due to the insufficient discrimination between living and dead cells. A further disadvantage is the extensive and time-consuming sample preparation, which frequently comprises a sample treatment and incubation with the corresponding DNA intercalator in the dark, inactivating the intercalator with light having a specific wavelength and DNA isolation in order to remove residues of the intercalating dyes, before the actual PCR, for example, real-time PCR, can be carried out, since quantitative results are almost always the matter of interest. Furthermore, DNA intercalating dyes generally have to be regarded as mutagenic, such that corresponding protection measures have to be carried out by the user. In addition, an expensive (real-time) thermocycler is necessary for an EMA-/PMA-PCR or similar methods, which may be a problem in particular for small laboratories.

WO 1996/014430 A1 and U.S. Pat. No. 6,146,834 disclose a method for the selective detection of living cells, for example, living bacteria, wherein in a first step the living cells to be analyzed are proliferated by plating on an agar medium to increase the number of cells. In a second step, the living cells are directly used in a PCR reaction, wherein no upstream extraction step for isolating the DNA from the cells is carried out. This method enables a selective detection of living cells by the first proliferation step, which exclusively reproduces living cells and of course does not proliferate dead cells.

However, it is a disadvantage of the method known from WO 1996/014430 A1 and U.S. Pat. No. 6,146,834 that the same do not enable a quantification of living cells of the original sample, since the cells are proliferated by cultivation before PCR. Furthermore, it is a disadvantage that a sufficient proliferation of the cells by cell division may last at least several hours to many days depending on the respective cells, which cannot be tolerated in analyses critical in terms of time. Furthermore, so-called VBNC (viable but non-culturable bacteria) are not detected in WO 1996/014430 A1 and U.S. Pat. No. 6,146,834. VBNC are bacteria which have reduced their metabolism by environmental influences to an extent such that they do not divide anymore, although the same are viable bacteria. In addition, only a small percentage of all bacterial species is cultivatable at all, and in this context many species are extremely demanding and only grow on specific nutrient media. According to current estimations, only 12% of all bacteria are cultivatable at all.

WO 1999/014359 A1 discloses a method for discriminating between living and dead microorganisms by insertion of genetic markers in the replicon of the microorganisms. This method is based on the generation of mRNA or cDNA from RNA as target substrate by a reverse transcriptase or a thermostable polymerase, wherein only the genetic markers of living cells are selectively detected.

As a disadvantage of the method described in WO 1999/014359 A1, long incubation periods, for example, overnight, are necessary for the amplification using the "plasmid-directed replication". This causes a proliferation of the microorganisms, such that according to the result no conclusions can be drawn with regard to the number of living cells in the original sample. Furthermore, in the framework of an RNA isolation, many potential sources of error exist, since RNA is much less stable than DNA, such that the efficiency in the framework of an RNA isolation is much less than in a DNA isolation. Furthermore, also the reverse transcriptase PCR is considerably less efficient than standard PCR methods.

WO 2002/052034 A1 and JP 2001/299399 A disclose a method for determining the ratio of dead to living cells in a sample, wherein a reverse transcriptase PCR is carried out with a reference sample, which exclusively exists of living cells, with a reference sample, which exclusively exists of dead cells, and with reference samples, which contain dead and living cells in known predetermined ratios, and a correlation between the respective proportion between dead and living cells and the result of the respective PCR reaction is established. After that the PCR result of a sample having an unknown ratio between dead and living cells can be assigned to the associated ratio of living to dead cells.

As a disadvantage of the method known from WO 2002/052034 A1 and JP 2001/299399 A, the efficiency of an RNA isolation and a reverse transcriptase PCR, respectively, is below the efficiency of corresponding DNA-based methods, such that quantitative results may involve large errors.

Furthermore, it is a disadvantage that the amount of RNA in a cell is dependent not only on whether a cell is living or dead, but also on the environmental conditions. For example, RNA will be hardly found in viable endospores, since they have reduced their metabolism to a large extent. Such cells would be evaluated to be dead, since similar to dead cells RNA is hardly detectable.

DE 10 2008 029 999 A1 discloses a PCR-based method named "splice-PCR", which is based on the following principle: In dead cells both the DNA transcription to RNA as well as the posttranscriptional modification of the primary RNA transcripts are disrupted. By a posttranscriptional modification, in particular by the "splicing" of introns, gene-specific sequence differences result between the genomic DNA, which forms the transcription template, and a double-stranded complementary DNA (cDNA) generated from the modified RNA by reverse transcription. Since genomic DNA is present both in living and dead cells, however, spliced DNA is present in living cells only, the described method is able to detect the presence of living cells due to sequence differences.

Disadvantages resulting from DE 10 2008 029 999 A1 are such that the described method does not provide quantitative results, but merely a qualitative statement with regard to the presence of living cells, since large differences with regard to the amount of RNA may occur dependent on the phase of the lifetime of the analyzed cells. For example, there is only a very small extent of metabolism in spores, such that detectable RNA is hardly present or is not present at all. Furthermore, also the error-prone handling of RNA in the isolation of RNA and the reverse transcription reaction has a negative impact on the sensitivity of detection. In addition, it is also a disadvantage that said method can often determine the presence of living cells only for one specific target organism in the framework of a single assay, since the intron-exon structure for a gene is fluctuating very strongly from organism to organism, such that for example all-purpose bacterial primers cannot be used.

Thus, the object underlying the present invention is to provide a method enabling a quick, quantitative, sensitive as possible and comparatively cheap differentiation between living and dead cells for use in pharmaceutical, medical, food technological and similar fields.

This object is achieved by the embodiments characterized in the claims.

In particular, a subject-matter of the present invention relates to a method for quantitatively determining living and dead cells in a biological sample, comprising the steps of:
(a) providing an untreated aliquot of the sample,
(b) providing an aliquot of the sample, wherein all cells have been inactivated,
(c) carrying out a DNA amplification reaction with the aliquots provided in steps (a) and (b), respectively, wherein the DNA amplification reaction does not impair the membrane integrity of living cells,
(d) determining the respective DNA amount in the aliquots by the DNA amplification reactions carried out in step (c), and
(e) determining the number of living and dead cells in the biological sample from the amounts of DNA determined in step (d).

In this context, the term "quantitative determination" relates to the determination of the number of living and dead cells in a sample. The number of cells is designated as N, however, may also be designated as GE (genome units), since a genome corresponds to a cell. For example, in the following the number of living cells can be designated both as $N_{living}$ and as $GE_{living}$.

The biological sample, in which the number of living and dead cells is determined by the method according to the present invention, is not subject to any specific limitations and comprises any samples, wherein cells of any kind, for example, prokaryotic cells, may be present. For example, biological samples may be any medical, pharmaceutical or food technological samples. The biological sample and/or the aliquots formed thereof may optionally be concentrated before their further processing.

The untreated aliquot of the sample provided in step (a) of the method according to the present invention may be used directly and without any pretreatment. In particular, said aliquot is not subjected to any treatment or substance, which may impair the cells and their membrane integrity, respectively.

All cells are completely inactivated in the aliquot of the sample provided in step (b). Suitable methods for the complete inactivation of cells are not subject to any specific limitations and are known in the prior art. For example, they comprise any methods, which on the one hand result in a complete loss of integrity of the cell membranes, and on the other hand do not impair the subsequent steps of the method according to the present invention. In a concrete example, the cells are inactivated by an ultrasound treatment, for example, for 10 minutes. In a specific embodiment within the framework of inactivating the cells, the DNA of the cells is extracted and in step (c) of the method according to the present invention said DNA is introduced into the corresponding DNA amplification reaction. Methods for the extraction of DNA from cells are known in the prior art.

The DNA amplification reaction carried out in step (c) of the method according to the present invention does not impair the membrane integrity of living cells. Corresponding methods are not subject to specific limitations and are known in the prior art. Methods carried out at a temperature of below 50° C., preferably between 36 and 42° C., and which are non-isothermal, however, preferably isothermal, i.e., are carried out at a constant temperature, are preferred. According to a preferred embodiment, the DNA amplification reaction is a recombinase-polymerase-amplification (RPA). The same is known in the prior art.

The determination of the respective amount of DNA in the aliquots of step (d) of the method according to the present invention may be carried out with the aid of fluorescence-labeled probes, which specifically bind to the amplified DNA, or with the aid of DNA-binding fluorescence dyes, like, for example, "SYBR Green I". In this case, the determination of the respective amount of DNA is carried out with the aid of a fluorometer, for example, a real-time fluorometer. Corresponding methods for generating and determining fluorescence-labeled amplification products are known in the prior art. According to a practical example, the DNA amplification reaction may be carried out in the presence of a DNA-binding fluorescence dye, wherein the generated fluorescence is measured in regular intervals, for example, every 30 seconds. In this way, fluorescence curves may be established, wherein the fluorescence intensity is illustrated in a time-dependent manner. The duration until the fluorescence intensity reaches a specific threshold value may be used as a measure for the amount of DNA originally present in the sample or in the respective aliquot.

Alternatively, the determination of the respective amount of DNA in the aliquots in step (d) of the method according to the present invention may be carried out with the aid of suitable endpoint analysis methods. For example, after the DNA amplification reaction has been carried out, a gel electrophoresis may be carried out and a comparison or quantification of the band intensities may be carried out. Suitable endpoint analysis methods and methods for gel electrophoresis and quantifying corresponding bands are known in the prior art.

Preferably, the determination of the number of living and dead cells in the biological sample is carried out in step (e) of the method according to the present invention by a standard curve, which is obtained by DNA amplification reactions with parallel reaction batches containing known DNA concentrations. In this way, for example, parallel reaction batches can be used, from which it is known how many cells correspond to the respective contained amount of DNA. In this way, the amounts of DNA determined in the two aliquots used in the method according to the present invention or the parameters corresponding to the same, for example, the time period until a specific fluorescence intensity value is reached during the DNA amplification reaction, may be correlated with a corresponding number of cells.

In this context, the determination of the number of living cells in the biological sample in step (e) of the method according to the present invention is carried out according to the formula $N_{living}=N_{total}-N_{dead}$, or according to the equivalent formula $GE_{living}=GE_{total}-GE_{dead}$, wherein $N_{total}$ and $GE_{total}$, respectively, are determined by the amount of DNA determined in step (d) in the aliquot provided in step (b), and $N_{dead}$ is determined by the amount of DNA determined in step (d) in the aliquot provided in step (a). In the above-mentioned formulae, N designates a number of cells and GE designates the number of genome units, wherein one genome unit corresponds to one cell. $N_{living}$ designates the number of living cells in the sample, $N_{total}$ the total number of cells irrespective of whether the same are living or dead, and $N_{dead}$ the number of dead cells in the sample.

The object underlying the present invention is achieved in that the quantitative differentiation between living and dead cells is carried out with the aid of an isothermal DNA amplification reaction or with a DNA amplification reaction, which does not impair the membrane integrity of the cells to be detected. There are different methods for isothermal DNA amplification. A method suitable for the application described herein is RPA, since it is carried out at temperatures below 50° C., preferably at a constant temperature of 36 to 42° C., and thus does not result in an inactivation of the cells. By comparison, the denaturation step at 95° C. in a conventional PCR inactivates cells almost completely. Nevertheless, almost any DNA amplification method is suitable, which provides an amplification at temperatures below 50° C., preferably at a constant temperature of about 36 to 42° C., and does not initiate any other cell-inactivating processes. For the majority of all cells, in particular all microorganisms, said temperature range provides ideal conditions in order to maintain viability of the intact cells of a sample during the amplification. In this way, cells are still vital also after amplification and only the DNA of dead cells having cell membranes, which are not intact anymore, is amplified, such that the amplification enzymes of the RPA reaction can enter the cell in order to reproduce the DNA.

The method according to the present invention comprises the following steps: The untreated or concentrated sample is directly introduced into the isothermal amplification, such that only the DNA of cells having a disturbed membrane integrity is accessible for the amplification and thus only the DNA of dead cells is amplified. In addition, a further isothermal amplification reaction with the same sample is carried out in parallel, wherein in this case the sample has been subjected to a DNA extraction or a complete inactivation, such that all cell membranes have lost their integrity and the complete DNA, i.e. both the DNA of the dead cells as well as of the living cells of the original sample, is reproduced.

If in the amplification a dilution series of quantified genomic DNA is run in parallel, a standard curve is obtained, by which both the number of all genome copies of the dead cells and the number of genome copies of the total of all cells can be calculated. Thus, the number of living bacteria in a sample may be determined as follows:

$GE_{living}=GE_{total}-GE_{dead}$

According to a preferred embodiment of the invention, fluorescence-labeled probes or fluorescence dyes, like, for example, "SYBR Green I", allow quantification and visualization of the results. No Ct values ("cycle threshold", threshold value cycle) are determined by using the RPA, as it is the case with real-time PCR, but the reaction times until the fluorescence exceeds a specific threshold value. Nevertheless, the principle on which the invention described herein is based, also works via an endpoint analysis using gel electrophoresis, wherein the thicknesses of bands of the gel are a measure for the amount of amplified DNA or detected cells.

The object underlying the present invention is further achieved in that the method, for example, of the isothermal RPA, is carried out within 10 to 30 minutes at a constant temperature, i.e. without requiring expensive real-time thermocyclers, and enables a differentiation between living and dead cells. The detection of the fluorescence signals may be carried out in a standard fluorometer, preferably in a real-time fluorometer, which is temperature-controllable in a constant manner and which can be purchased already at a fraction of the costs of a real-time thermocycler.

The possibility that a proliferation of the cells may occur during the amplification reaction, which would falsify the obtained results, does not have to be considered, since even fast-growing germs have a generation time of at least 20 minutes in the exponential phase, however, in this case at first pass through an adaptation phase (lag-phase) to the new "cultivating conditions" present during the amplification, such that there is no proliferation via cell division during this very short amplification reaction (10 to 30 min). In a further preferred embodiment of the present invention the amplification, for example, by RPA, is carried out at room temperature or at still lower temperatures, however, with reduced rate, wherein the proliferation of the bacteria is additionally suppressed during amplification in the desired manner.

A further decisive advantage of the invention is that only one of the two samples to be amplified has to be subject to a DNA extraction or a complete inactivation and the second sample is still vital after the amplification and may optionally be cultivated or subsequently used in a different manner.

The figures show:

FIG. 1: Target amplicon at 430 bp on agarose gel after completed RPA reaction.

Figure 2:
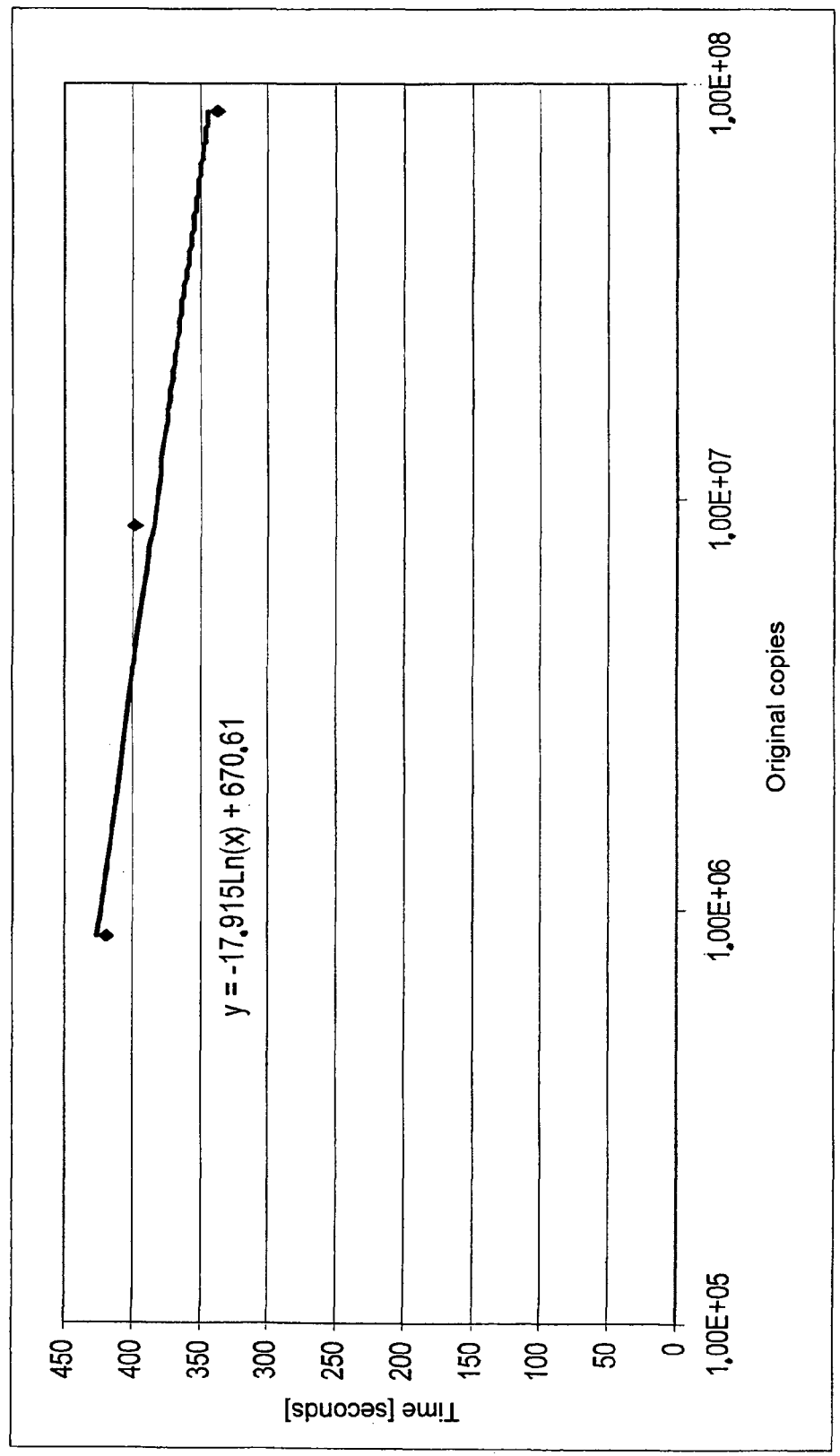

FIG. 2: Standard curve using quantified *E. coli* DNA.

Figure 3:
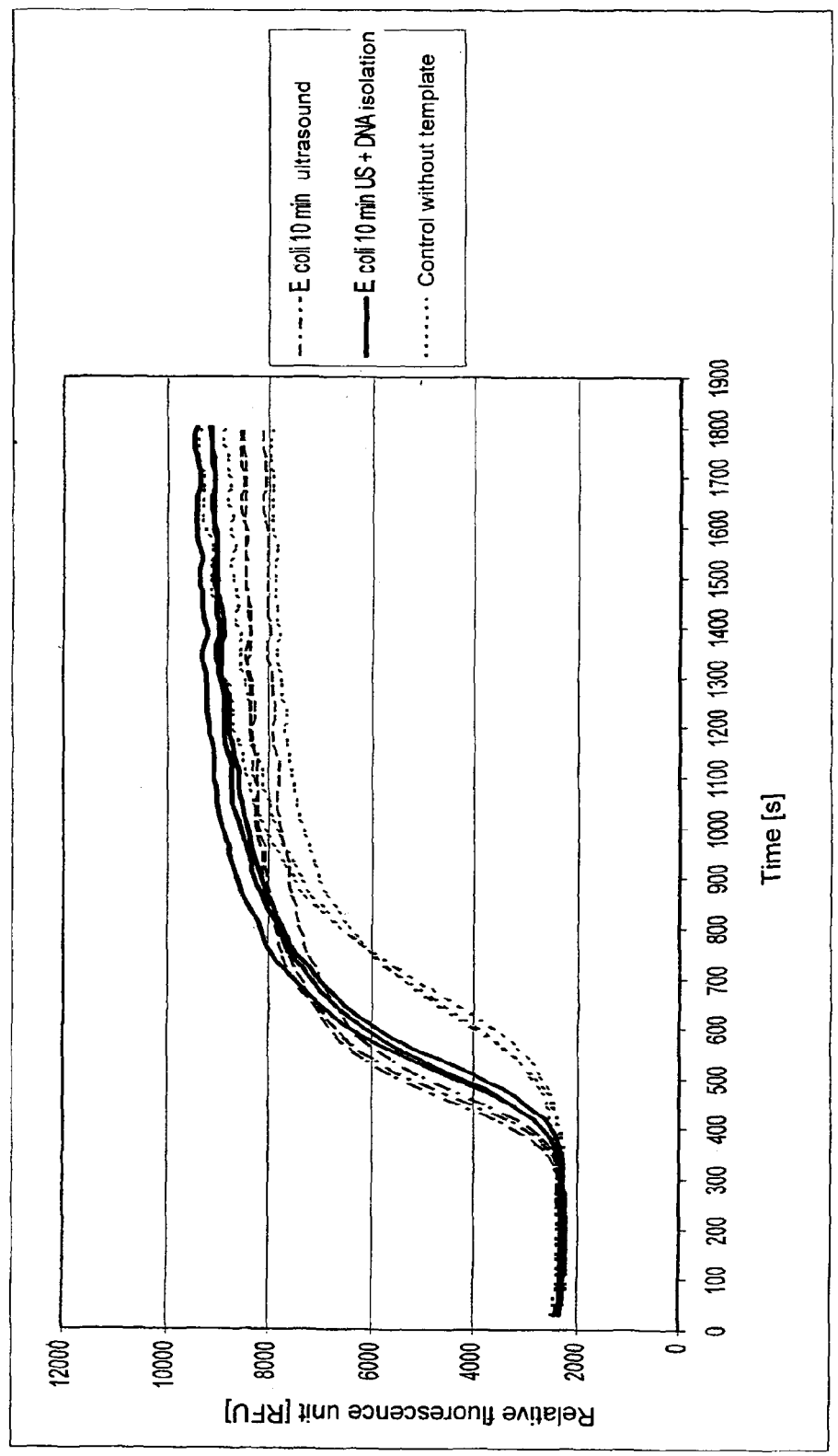

FIG. 3: Fluorescence curves of samples 1 and 2 as well as negative controls.

Figure 4:
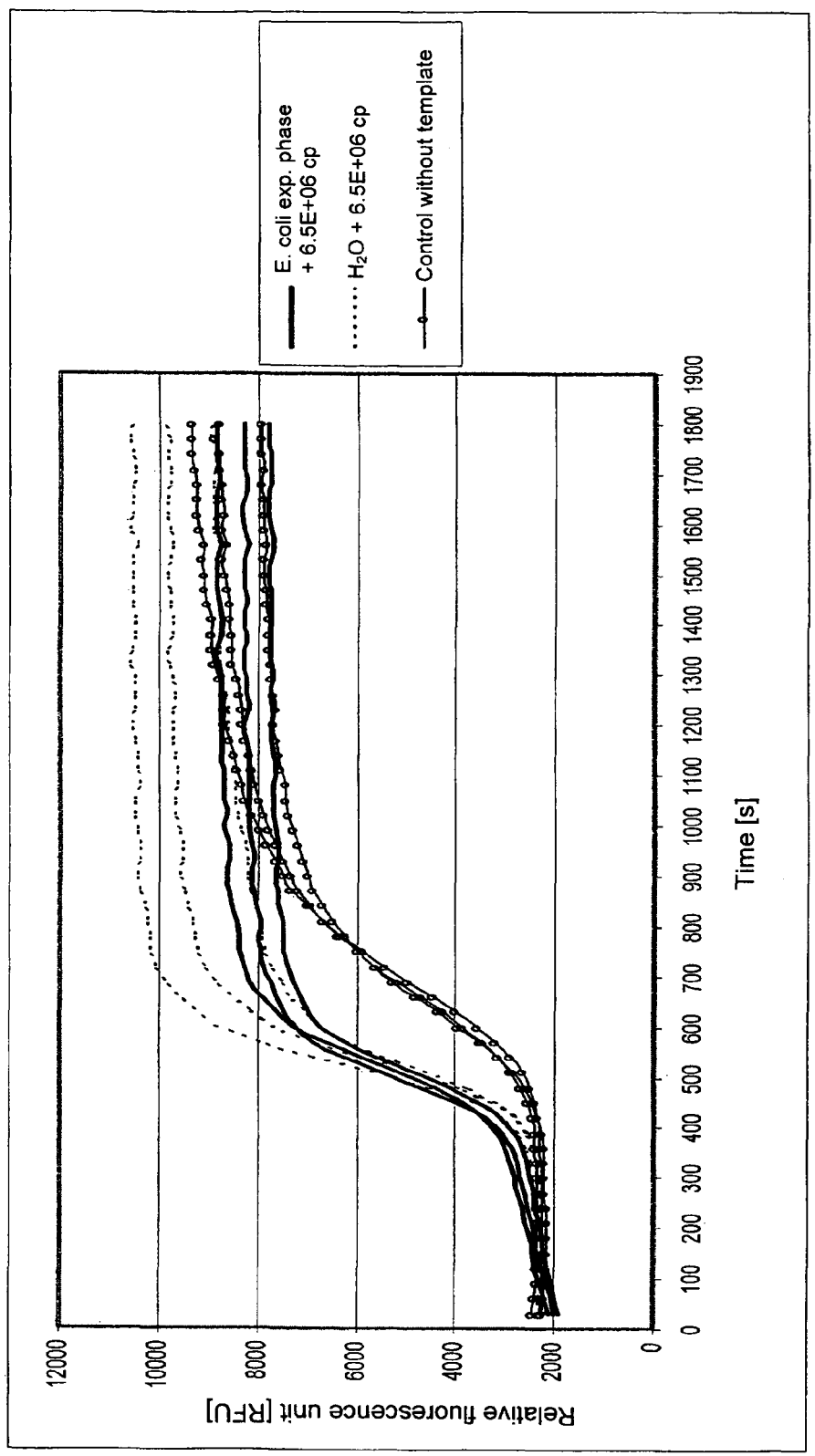

FIG. 4: Fluorescence curves of samples 3 and 4 as well as negative controls.

Figure 5:
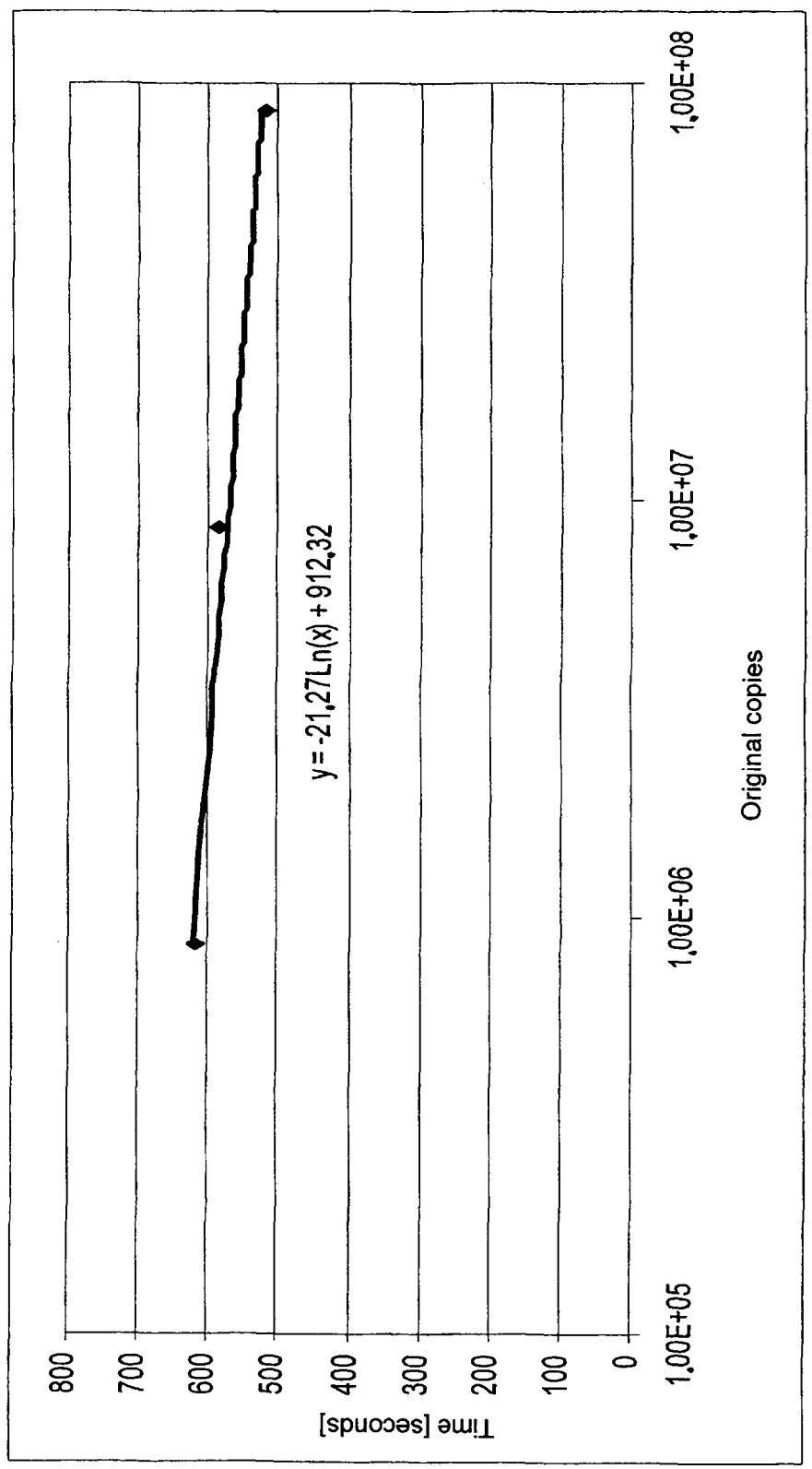

FIG. 5: Standard curve using quantified *E. coli* DNA.

Figure 6:
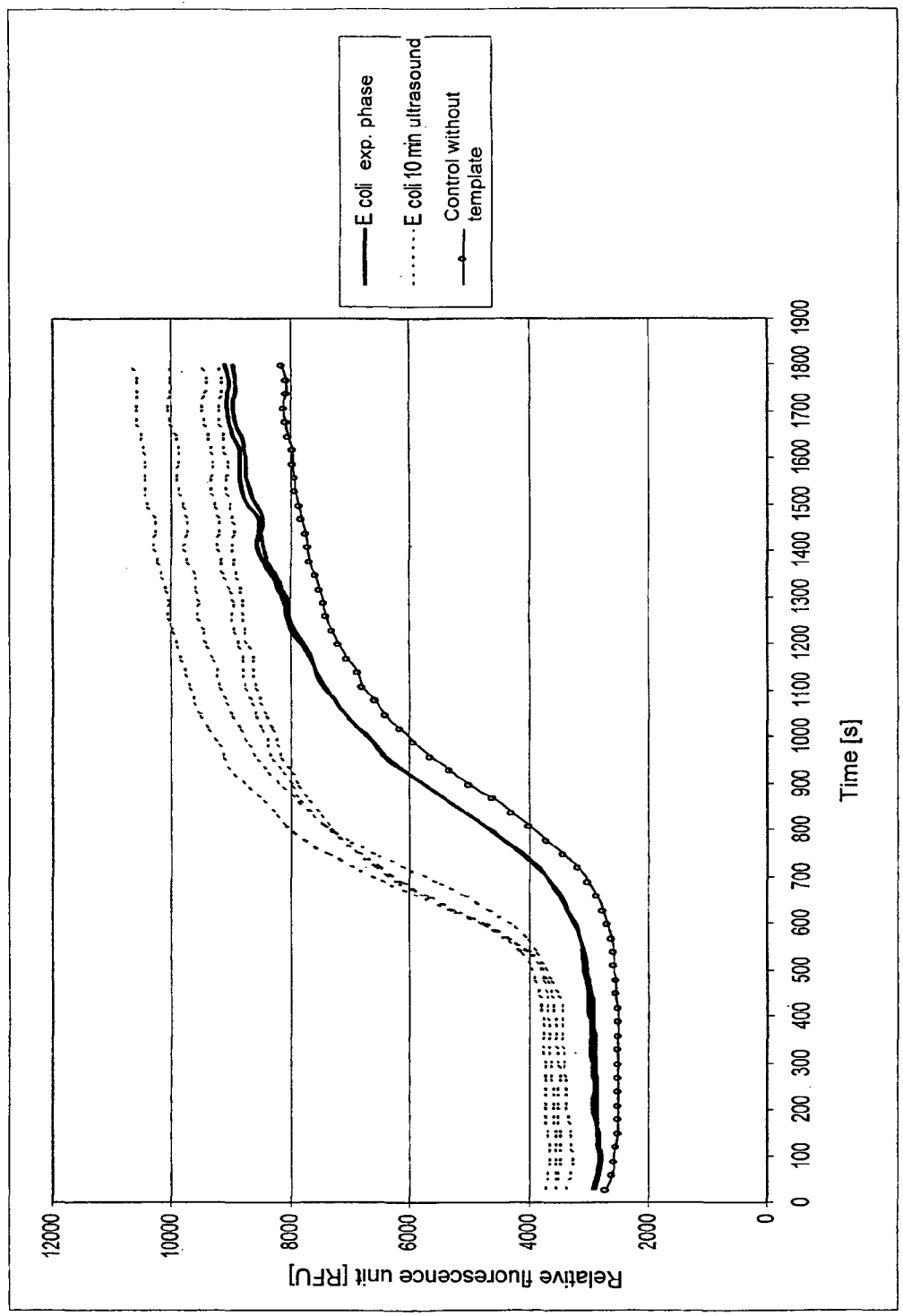

FIG. 6: Fluorescence curves of vital and inactivated *E. coli* cells as well as negative controls.

The present invention is illustrated in further detail by the following non-limiting examples.

EXAMPLE 1

A reaction batch according to the present invention comprises, for example, the following components:

200 µl reaction vessel with at least one recombinase, an SSB (single-stranded DNA-binding protein), a DNA polymerase, a "crowding agent" (e.g. polyethylene glycol), a buffer, a reductant, ATP or an ATP analogon, optionally a "recombinase loading protein", one or more primer(s), a target DNA, as well as magnesium ions.

The RPA kit "TwistAmp fpg" of the company TwistDx has been used, wherein a part of said components is already provided as a freeze-dried pellet in 200 µl reaction vessels. The user merely has to add buffer solution, the desired primer, the sample and magnesium acetate and optionally a detection probe, in order to complete the reaction batch.

In example 1, a 50 µl reaction batch has the following composition:
Lyophilized pellet of the RPA kit "TwistAmp fpg"
29.5 µl buffer of the RPA kit "TwistAmp fpg"
420 nM primer having the sequence:

(SEQ ID NO: 1)
5'-CAGGATTAGATACCCTGGTAGTCCACGCCGTAAAC-3'

420 nM primer having the sequence:

(SEQ ID NO: 2)
5'-TAAGGGGCATGATGATTTGACGTCATCCCCACCTT-3'

14.2 µl sample
12 mM magnesium acetate

An RPA reaction begins only after adding magnesium acetate, since magnesium ions are essential for the activity of the DNA polymerase.

In order to guarantee exactly the same start time for samples running in parallel, magnesium acetate is pipetted in the lid of the reaction vessels, such that the magnesium acetate can be simultaneously introduced in all samples by a brief centrifugation and thus all reactions start in parallel. A so-called "magnesium start" is necessary, since RPA reactions already run at room temperature, although with low efficiency.

In example 1 a *Bacillus subtilis* cultivation (in exponential phase) and an *Escherichia coli* cultivation (in exponential phase) were diluted 1:100 and each was directly used in an RPA reaction with the above-described reaction batch composition at 37° C. After a reaction time of 30 min the complete reaction batches (50 µl each) were plated on nutrient agar and incubated at 37° C. Both *E. coli* and *B. subtilis* formed a bacterial lawn within 24 hours.

Thus, according to example 1 it could be shown that also after the isothermal amplification both *B. subtilis* cells (gram positive) and *E. coli* cells (gram negative) are still vital and no inactivating substances or reactions are present during the amplification.

EXAMPLE 2

According to an embodiment of the present invention the band thicknesses after RPA and gel electrophoresis are evaluated in a qualitative manner.

As a sample material, the gram-negative bacterium *E. coli* both in the exponential phase and also after complete inactivation by ultrasound was used. As an example of a gram-positive species, *B. subtilis* was used in the stationary phase and after complete inactivation.

The experimental conditions were selected as follows:
30 min amplification at 37° C. with the following components per 50 µl reaction batch:
Lyophilized pellet of the RPA kit "TwistAmp fpg"
29.5 µl buffer of the RPA kit "TwistAmp fpg"
420 nM primer having the sequence:

(SEQ ID NO: 1)
5'-CAGGATTAGATACCCTGGTAGTCCACGCCGTAAAC-3'

420 nM primer having the sequence:

(SEQ ID NO: 2)
5'-TAAGGGGCATGATGATTTGACGTCATCCCCACCTT-3'

14.2 µl sample
12 mM magnesium acetate

After the finished amplification reaction the complete reaction batches were purified with the aid of a silica-based membrane for DNA isolation in the presence of chaotropic compounds for the subsequent agarose gel electrophoresis (FIG. 1).

In example 2 it could be shown that an *E. coli* cultivation in the exponential phase does not result in a DNA amplification (no bands on the agarose gel), since it is a 100% vital cultivation in the ideal case. Furthermore, it could demonstrated that a *B. subtilis* cultivation in the stationary phase results in thin DNA bands (amplicon at 430 bp), since a die off of cells already occurs in the stationary phase. As expected, previously inactivated *B. subtilis* and *E. coli* samples (10 min ultrasound), however, resulted in clearly thicker DNA bands at 430 bp.

EXAMPLE 3

Each of the following samples has been analyzed three times by RPA in a comparative manner, in order to demonstrate the quantification potential of the method according to the present invention.
1. *E. coli* (exponential phase) was completely inactivated by ultrasound for 10 min and then directly used in the RPA reaction.
2. *E. coli* (exponential phase) was completely inactivated by ultrasound for 10 min, the DNA was isolated with an extraction kit based on a silica membrane and then used in the RPA reaction.
3. A DNA spike of $6.5 \times 10^6$ genome units (GE) per RPA reaction of a quantified genomic *E. coli* DNA was added to *E. coli* (exponential phase) and then isothermally amplified.
4. A DNA spike of $6.5 \times 10^6$ genome units (GE) per RPA reaction of a quantified genomic *E. coli* DNA was added to water (PCR grade) and then isothermally amplified.

A standard curve with quantified genomic DNA and negative controls (controls without template; adding "PCR grade" water instead of the sample) were run in parallel in the RPA. The reaction ran at 37° C. within a time period of 30 min. Fluorescence data were recorded every 30 seconds.

A 50 µl reaction batch contained the following components:
Lyophilized pellet of the RPA kit "TwistAmp fpg"
29.5 µl buffer of the RPA kit "TwistAmp fpg"
420 nM primer having the sequence:

(SEQ ID NO: 1)
5'-CAGGATTAGATACCCTGGTAGTCCACGCCGTAAAC-3'

420 nM primer having the sequence:

(SEQ ID NO: 2)
5'-TAAGGGGCATGATGATTTGACGTCATCCCCACCTT-3'

1 µl "SYBR Green I" (diluted 1:50,000)
13.2 µl sample
12 mM magnesium acetate

The standard curve as well as the corresponding values are shown in FIG. 2 and table 1.

TABLE 1

Values of the standard curve using quantified E. coli DNA

| Quantified DNA standard | Time until increase of fluorescence [seconds] (average, n = 2) | Concentration [Copies/reaction] |
|---|---|---|
| E. coli standard diluted 1:10 | 337 | $8.58 \times 10^7$ |
| E. coli standard diluted 1:100 | 398 | $8.58 \times 10^6$ |
| E. coli standard diluted 1:1000 | 419 | $8.58 \times 10^5$ |

The values obtained for samples 1 to 4 and fluorescence curves are shown in FIGS. 3 and 4 as well as in table 2.

TABLE 2

Determined concentrations of the genome units per reaction

| Sample | Time until increase of fluorescence [seconds] | Concentration [Copies/reaction] |
|---|---|---|
| E. coli 10 min ultrasound (1) | 378<br>368<br>375 | $1.62 \times 10^7$ |
| E. coli 10 min ultrasound + DNA isolation (2) | 420<br>403<br>404 | $2.35 \times 10^6$ |
| E. coli exponential phase + $6.5 \times 10^6$ GE (3) | 408<br>416<br>422 | $1.62 \times 10^6$ |
| $H_2O + 6.5 \times 10^6$ GE (4) | 398<br>412<br>408 | $2.77 \times 10^6$ |
| Control without template | 509<br>491<br>486 | $2.06 \times 10^4$ |

The results in table 2 as well as in FIGS. 3 and 4 demonstrate that the present invention allows a quantitative differentiation between living and dead microorganisms.

Regarding the curve progression and the determined concentration of genome units, only a small difference is apparent between samples 1 and 2, which can be explained by the DNA losses in the silica membrane-based DNA isolation carried out in sample 2. However, this approach has shown that DNA of bacteria having a disturbed membrane integrity may be completely reproduced by RPA.

The curve progressions of samples 3 and 4 (FIG. 4) as well as the determined concentrations of genome units (copies/reaction; table 2) are almost identical, which illustrates that vital cells remain intact during an RPA reaction and that their DNA is not amplified.

The negative controls ("controls without template" in FIGS. 3 and 4 as well as in table 2) also show signals in the framework of the fluorescence detection. However, the same could be clearly differentiated from the samples and thus were not considered. These signals in the negative controls are the result of non-specific amplifications, for example, primer artifacts, since the non-specific dye "SYBR Green I" has been used for the detection in these experiments. A primer screening in further experiments, which is adapted to the respective application, allows to select optimal primer sequences for the respective target application. Furthermore, specific fluorescence-labeled probes may be used instead of "SYBR Green I" in order to avoid signals in the negative controls.

EXAMPLE 4

Both completely vital as well as inactivated E. coli samples each have been analyzed four times by RPA and the number of living cells has been determined in parallel by plating on nutrient agar in different dilution stages (determination of colony numbers after an incubation time of 24 hours at 37° C.).

A standard curve with quantified genomic DNA and a negative control (control without template; adding "PCR grade" water instead of the sample) were run in parallel in the RPA. Fluorescence data were recorded during 30 min at a constant reaction temperature of 37° C. every 30 seconds.

A 50 μl reaction batch contained the following components

Lyophilized pellet of the RPA kit "TwistAmp fpg"
29.5 μl buffer of the RPA kit "TwistAmp fpg"
420 nM primer having the sequence:

(SEQ ID NO: 1)
5'-CAGGATTAGATACCCTGGTAGTCCACGCCGTAAAC-3'

420 nM primer having the sequence:

(SEQ ID NO: 2)
5'-TAAGGGGCATGATGATTTGACGTCATCCCCACCTT-3'

1 μl "SYBR Green I" (diluted 1:50,000)
13.2 μl sample
12 mM magnesium acetate

The standard curve as well as the corresponding values are shown in FIG. 5 and table 3.

TABLE 3

Values of the standard curve using quantified E. coli DNA

| Quantified DNA standard | Time until increase of fluorescence [seconds] (average, n = 2) | Concentration [Copies/reaction] |
|---|---|---|
| E. coli standard diluted 1:10 | 517 | $8.58 \times 10^7$ |
| E. coli standard diluted 1:100 | 586 | $8.58 \times 10^6$ |
| E. coli standard diluted 1:1000 | 615 | $8.58 \times 10^5$ |

The values obtained for the samples and fluorescence curves are shown in FIG. 6 as well as in table 4.

TABLE 4

Determined concentrations of the genome units (number of cells) per reaction and per ml

| Sample | Time until increase of Fl [seconds] | Concentration [Copies/reaction] | Average concentration [Copies/reaction] | Average concentration [Copies/ml] |
|---|---|---|---|---|
| E. coli 10 min ultrasound = $GE_{total}$ | 526<br>527<br>549<br>583 | $7.87 \times 10^7$<br>$7.34 \times 10^7$<br>$2.66 \times 10^7$<br>$5.25 \times 10^6$ | $4.60 \times 10^7$ | $3.48 \times 10^9$ |
| E. coli exponential phase = $GE_{dead}$ | 665<br>636<br>656<br>662 | $1.15 \times 10^5$<br>$4.32 \times 10^5$<br>$1.73 \times 10^5$<br>$1.27 \times 10^5$ | $2.12 \times 10^5$ | $1.60 \times 10^7$ |
| Control without template | 677 | $6.53 \times 10^4$ | | |

The following results with regard to the number of living cells in the sample ($R_{living}$) and for the corresponding number of genome units ($GE_{living}$):

$$GE_{living} = GE_{total} - GE_{dead} = 3.48 \times 10^9 - 1.60 \times 10^7 = 3.47 \times 10^9 \text{ GE/ml}$$

The data from table 4 show that the E. coli culture in the exponential phase contained $3.47 \times 10^9$ living cells per milliliter and only 1.60×10⁷ dead bacteria, corresponding to 0.46%. The associated fluorescence curves are shown in FIG. 6.

The parallel plating on nutrient agar resulted in lower, however, feasible results, since it has to be assumed that there are at no time 100% of the living bacteria growing and forming colonies, since, for example, VBNC may be present. Many bacteria change to a VBNC phase, for example, in case of unfavorable environmental conditions. The metabolism is reduced, such that the growth on standard nutrient agar is not possible anymore. Furthermore, it has to be considered that a colony frequently has not grown from a single germ of the original sample, but has to be ascribed to several not completely separated microorganisms. A number of living cells of *E. coli* in the exponential phase of about 5.0×10⁸ bacteria per milliliter has been determined by plating.

The invention claimed is:

1. A method for quantitatively determining the number of living and dead cells in a biological sample, comprising the steps of:
   (a) providing an untreated aliquot of the sample,
   (b) providing an aliquot of the sample, wherein all cells have been inactivated, resulting in a complete loss of integrity of the cell membranes,
   (c) carrying out separate DNA amplification reactions with the aliquots provided in steps (a) and (b), respectively, wherein the DNA amplification reactions do not impair the membrane integrity of living cells,
   (d) determining the respective DNA amount in the aliquots by the DNA amplification reactions carried out in step (c), and
   (e) determining the number of living and dead cells in the biological sample from the amounts of DNA determined in step (d).

2. The method according to claim 1, wherein the DNA amplification reactions are isothermal amplification reactions.

3. The method according to claim 1, wherein the DNA amplification reactions are isothermal or non-isothermal amplification reactions, which run at temperatures below 50° C.

4. The method according to claim 3, wherein the DNA amplification reactions run at a temperature between 36 and 42° C.

5. The method according to claim 1, wherein the DNA amplification reactions are recombinase polymerase amplification reactions.

6. The method according to claim 1, wherein in the inactivation of the cells of the aliquot provided in step (b) the DNA of these cells is extracted, and wherein in step (c) said DNA is used in the corresponding DNA amplification reaction.

7. The method according to claim 1, wherein the determination of the respective amount of DNA in step (d) is carried out using fluorescence-labeled probes or DNA-binding fluorescent dyes.

8. The method according to claim 7, wherein the determination of the respective amount of DNA in step (d) is carried out using a fluorometer.

9. The method according to claim 8, wherein the fluorometer is a real-time fluorometer.

10. The method according to claim 1, wherein the determination of the respective amount of DNA in step (d) is carried out using gel electrophoresis and a subsequent comparison of the band intensities.

11. The method according to claim 1, wherein the determination of the number of living and dead cells in the biological sample in step (e) is carried out with the aid of a standard curve, which is obtained by DNA amplification reactions with parallel reaction batches containing known DNA concentrations.

12. The method according to claim 1, wherein the cells are prokaryotic cells.

* * * * *